(12) United States Patent
Polo et al.

(10) Patent No.: US 10,101,675 B2
(45) Date of Patent: Oct. 16, 2018

(54) METROLOGY APPARATUS, METHOD OF MEASURING A STRUCTURE AND LITHOGRAPHIC APPARATUS

(71) Applicant: ASML Netherlands B.V., Veldhoven (NL)

(72) Inventors: Alessandro Polo, Delft (NL); Simon Gijsbert Josephus Mathijssen, Rosmalen (NL)

(73) Assignee: ASML Netherlands B.V., Veldhoven (NL)

( * ) Notice: Subject to any disclaimer, the term of this patent is extended or adjusted under 35 U.S.C. 154(b) by 17 days.

(21) Appl. No.: 15/444,765

(22) Filed: Feb. 28, 2017

(65) Prior Publication Data

US 2017/0255104 A1 Sep. 7, 2017

(30) Foreign Application Priority Data

Mar. 1, 2016 (EP) ..................................... 16158109

(51) Int. Cl.
*G03F 9/00* (2006.01)
*G03F 7/20* (2006.01)
(Continued)

(52) U.S. Cl.
CPC ............ *G03F 9/7046* (2013.01); *G01B 11/00* (2013.01); *G01B 11/02* (2013.01); *G01B 11/272* (2013.01);
(Continued)

(58) Field of Classification Search
CPC ....... G01B 11/00; G01B 11/02; G01B 11/272; G01B 11/303; G01N 21/9501;
(Continued)

(56) References Cited

U.S. PATENT DOCUMENTS 9,518,916 B1* 12/2016 Pandev ................ G01N 21/255
2003/0204326 A1* 10/2003 Opsal ..................... G01B 11/24
702/28
(Continued)

FOREIGN PATENT DOCUMENTS

WO WO 2009/078708 A1 6/2009
WO WO 2009/106279 A1 9/2009

OTHER PUBLICATIONS

Miyakawa et al., "Coded aperture detector: an image sensor with sub 20-nm pixel resolution," Optical Society of America, Optics Express, vol. 22, No. 16, Aug. 11, 2014; 7 pages.
(Continued)

*Primary Examiner* — Michelle M Iacoletti
(74) *Attorney, Agent, or Firm* — Sterne, Kessler, Goldstein & Fox P.L.L.C.

(57) ABSTRACT

Disclosed is a metrology apparatus and method for measuring a structure formed on a substrate by a lithographic process. The metrology apparatus comprises an illumination system operable to provide measurement radiation comprising a plurality of wavelengths; and a hyperspectral imager operable to obtain a hyperspectral representation of a measurement scene comprising the structure, or a part thereof, from scattered measurement radiation subsequent to the measurement radiation being scattered by the structure.

20 Claims, 3 Drawing Sheets

(51) Int. Cl.
*G01B 11/27* (2006.01)
*G01B 11/30* (2006.01)
*G01B 11/00* (2006.01)
*G01B 11/02* (2006.01)
*G01N 21/95* (2006.01)

(52) U.S. Cl.
CPC ....... *G01B 11/303* (2013.01); *G01N 21/9501* (2013.01); *G03F 7/7085* (2013.01); *G03F 7/70625* (2013.01); *G03F 7/70633* (2013.01); *G03F 7/70775* (2013.01); *G03F 9/7069* (2013.01); *G03F 9/7088* (2013.01); *G02B 2207/129* (2013.01)

(58) Field of Classification Search
CPC ........... G02B 2207/129; G03F 7/70625; G03F 7/70633; G03F 7/70775; G03F 7/7085; G03F 9/7046; G03F 9/7069; G03F 9/7088
See application file for complete search history.

(56) References Cited

U.S. PATENT DOCUMENTS

| | | | |
|---|---|---|---|
| 2006/0033921 | A1 | 2/2006 | Den Boef et al. |
| 2006/0164649 | A1 | 7/2006 | Rosengaus |
| 2009/0296075 | A1 | 12/2009 | Hu et al. |
| 2011/0027704 | A1 | 2/2011 | Cramer et al. |
| 2011/0043791 | A1 | 2/2011 | Smilde et al. |
| 2011/0102753 | A1 | 5/2011 | Van De Kerkhof et al. |
| 2012/0242970 | A1 | 9/2012 | Smilde et al. |
| 2013/0003068 | A1 | 1/2013 | Krishnan et al. |
| 2016/0025648 | A1 | 1/2016 | Duffy et al. |
| 2017/0076440 | A1* | 3/2017 | Pandev ................ G01N 21/255 |

OTHER PUBLICATIONS

Wagadarikar et al., "Single disperser design for coded aperture snapshot spectral imaging," Optical Society of America, Applied Optics, vol. 47, No. 10, Apr. 1, 2008; pp. B44-B51.
Bioucas-Dias et al., "A New TwIST: Two-Step Iterative Shrinkage/ Thresholding Algorithms for Image Restoration," IEEE Transactions on Image Processing, vol. 16, No. 12, Dec. 2007; pp. 2992-3004.
Wagadarikar et al., "Video rate spectral imaging using a coded aperture snapshot spectral imager," Optical Society of America, Optics Express, vol. 17, No. 8, Apr. 13, 2009; pp. 6368-6388.
Gehm et al., "Single-shot compressive spectral imaging with a dual-disperser architecture," Optical Society of America, Optics Express, vol. 15, No. 21, Oct. 17, 2007; pp. 14013-14027.
"Coded Aperture Snapshot Spectral Imaging (CASSI)," Duke Imaging and Spectroscopy Program, retrieved from http://www.disp.duke.edu/projects/CASSI/index.ptml, last updated Jun. 2, 2009; 4 pages.
International Search Report and Written Opinion of the International Searching Authority directed to related International Patent Application No. PCT/EP2017/052690, dated Jul. 5, 2017; 16 pages.
Lu, Liyang, "Imaging Plasmons with Compressive Hyperspectral Microscopy," Master of Science Thesis, Rice University, May 2015; 54 pages.

* cited by examiner

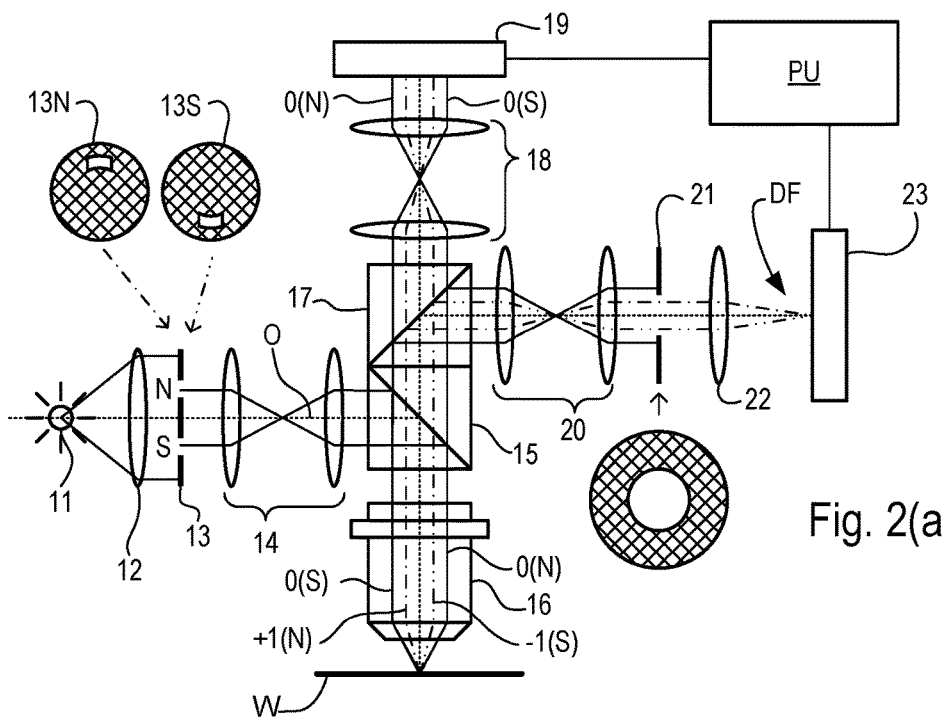
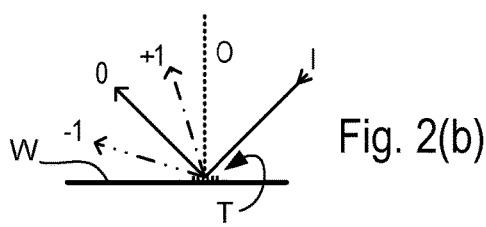
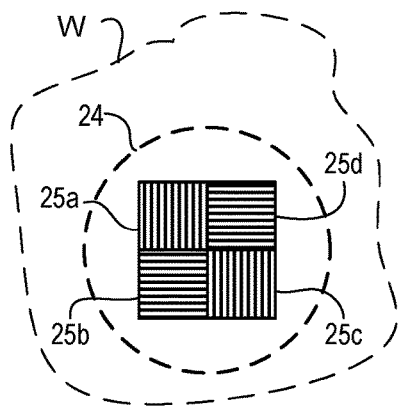
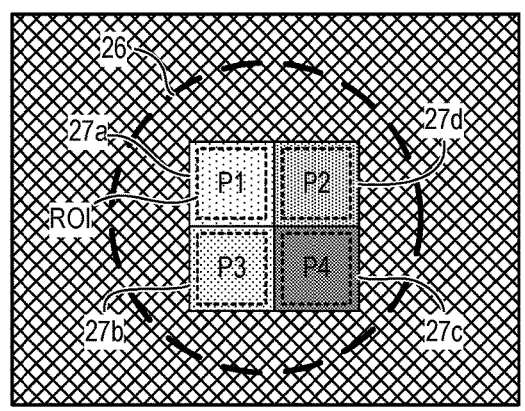
Fig. 2(a)
Fig. 2(b)
Fig. 2(c)
Fig. 2(d)

METROLOGY APPARATUS, METHOD OF MEASURING A STRUCTURE AND LITHOGRAPHIC APPARATUS

BACKGROUND

Field of the Invention

The present invention relates to methods and apparatus of lithography usable, for example, in the manufacture of devices by lithographic techniques and to methods of manufacturing devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of the accuracy of alignment of two layers in a device. Overlay may be described in terms of the degree of misalignment between the two layers, for example reference to a measured overlay of 1 nm may describe a situation where two layers are misaligned by 1 nm.

Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

The targets used by conventional scatterometers are relatively large, e.g., 40 μm by 40 μm, gratings and the measurement beam generates a spot that is smaller than the grating (i.e., the grating is underfilled). This simplifies mathematical reconstruction of the target as it can be regarded as infinite. However, in order to reduce the size of the targets, e.g., to 10 μm by 10 μm or less, e.g., so they can be positioned in amongst product features, rather than in the scribe lane, metrology has been proposed in which the grating is made smaller than the measurement spot (i.e., the grating is overfilled). Typically such targets are measured using dark field scatterometry in which the zeroth order of diffraction (corresponding to a specular reflection) is blocked, and only higher orders processed. Examples of dark field metrology can be found in international patent applications WO 2009/078708 and WO 2009/106279 which documents are hereby incorporated by reference in their entirety. Further developments of the technique have been described in patent publications US20110027704A, US20110043791A and US20120242970A. The contents of all these applications are also incorporated herein by reference. Diffraction-based overlay using dark-field detection of the diffraction orders enables overlay measurements on smaller targets. These targets can be smaller than the illumination spot and may be surrounded by product structures on a wafer. Targets can comprise multiple gratings which can be measured in one image.

In the known metrology technique, overlay measurement results are obtained by measuring an overlay target twice under certain conditions, while either rotating the overlay target or changing the illumination mode or imaging mode to obtain separately the $-1^{st}$ and the $+1^{st}$ diffraction order intensities. The intensity asymmetry, a comparison of these diffraction order intensities, for a given overlay target provides a measurement of target asymmetry, that is asymmetry in the target. This asymmetry in the overlay target can be used as an indicator of overlay error (undesired misalignment of two layers).

Metrology apparatuses, when performing such dark field scatterometry, presently can only perform measurements using measurement radiation of a single wavelength at any one time. However, different targets in different layers may show different behavior to different wavelength measurement radiation, which can result in variable measurement quality. Measurement radiation should be individually tuned to a target and/or layer. It would be desirable to be able to perform such measurements with measurement radiation of multiple wavelengths.

SUMMARY OF THE INVENTION

The invention in a first aspect provides a metrology apparatus for measuring a structure formed on a substrate by a lithographic process, said metrology apparatus comprising: an illumination system operable to provide measurement radiation comprising a plurality of wavelengths; and a hyperspectral imager operable to obtain a hyperspectral representation of a measurement scene comprising the structure, or a part thereof, from scattered measurement radiation subsequent to said measurement radiation being scattered by said structure.

The invention in a second aspect provides a method of measuring a structure formed on a substrate by a lithographic process comprising: illuminating the structure with measurement radiation comprising a plurality of wavelengths, such that the measurement radiation is scattered by the structure; spatially modulating the scattered measurement radiation with a coded pattern to obtain coded measurement radiation; spectrally dispersing the coded measurement radiation to obtain a two-dimensional coded spatio-spectral projection; sensing the two-dimensional coded spatio-spectral projection; and estimating a hyperspectral representation of the structure from the two-dimensional coded spatio-spectral projection and knowledge of the coded pattern Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying drawings in which:

FIGS. 2(a)-2(d) comprise (a) a schematic diagram of a dark field scatterometer for use in measuring targets using a first pair of illumination apertures, (b) a detail of diffraction spectrum of a target grating for a given direction of illumination; (c) a depiction of a known form of multiple grating target and an outline of a measurement spot on a substrate; and (d) a depiction of an image of the target of FIG. 2(c) obtained in the scatterometer of FIG. 2(a)

DETAILED DESCRIPTION OF EXEMPLARY EMBODIMENTS

Before describing embodiments of the invention in detail, it is instructive to present an example environment in which embodiments of the present invention may be implemented.

Figure 1:
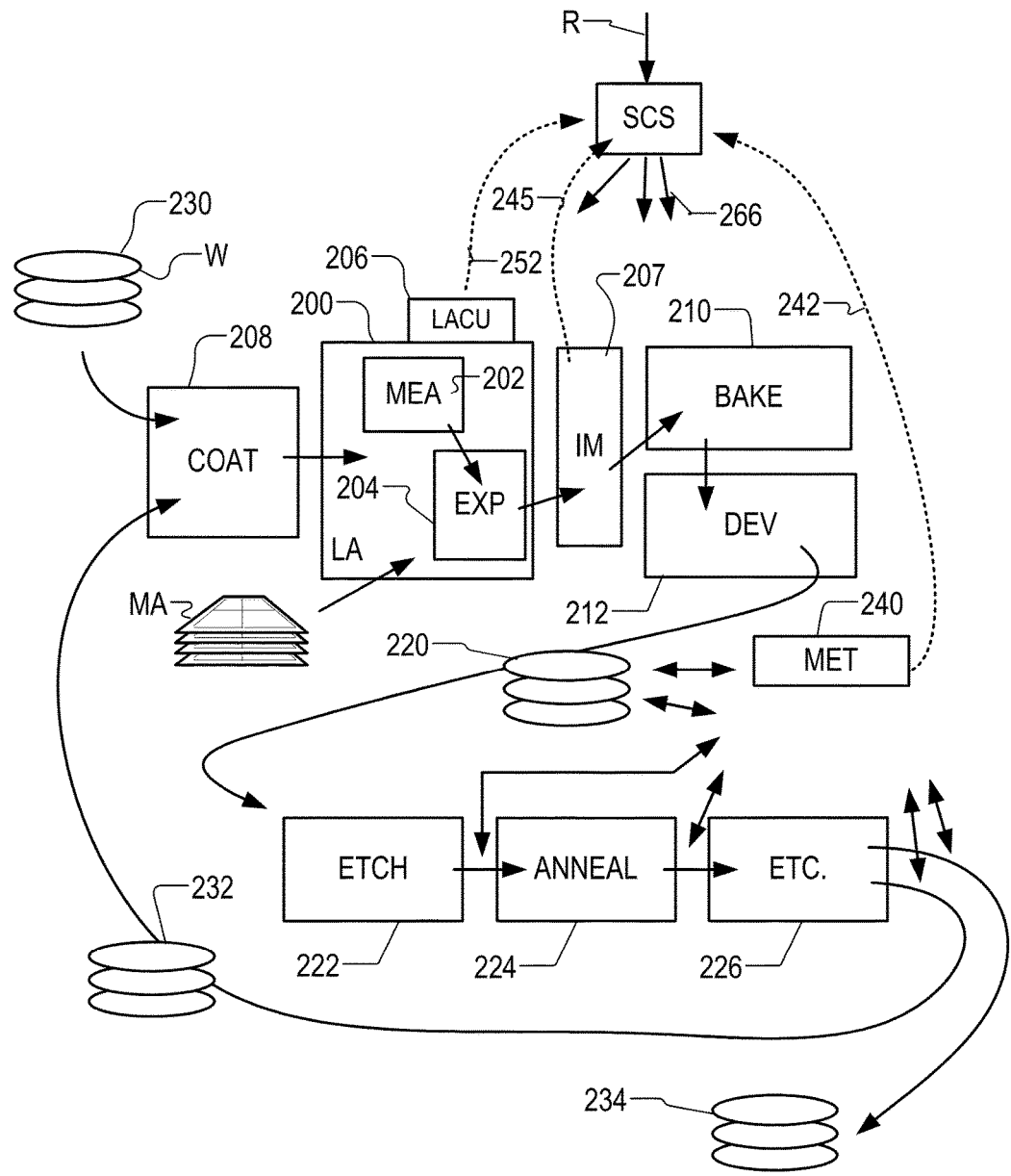
FIG. 1 depicts a lithographic apparatus together with other apparatuses forming a production facility for semiconductor devices.

FIG. 1 at 200 shows a lithographic apparatus LA as part of an industrial facility implementing a high-volume, lithographic manufacturing process. In the present example, the manufacturing process is adapted for the manufacture of semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example is of a so-called dual stage type which has two substrate tables and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located may also include one or more metrology systems. The metrology systems may include a stand-alone metrology apparatus MET 240 and/or an integrated metrology apparatus IM 207. The stand-alone metrology apparatus MET 240 receives some or all of the substrates W that have been processed in the litho cell for performing measurements offline. The integrated metrology apparatus IM 207 performs inline measurements and is integrated into the track to receive and measure some or all of the substrates W immediately after exposure. Metrology results are provided directly or indirectly to the supervisory control system (SCS) 238. If errors are detected, adjustments may be made to exposures of subsequent substrates, especially if the metrology can be done soon and fast enough that other substrates of the same batch are still to be exposed.

A common example of a metrology apparatus in a modern lithographic production facility is a scatterometer, for example an angle-resolved scatterometer or a spectroscopic scatterometer, and it may normally be applied to measure properties of the developed substrates at 220 prior to etching in the apparatus 222. Using stand-alone metrology apparatus 240 and/or integrated metrology apparatus 207, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. As is also well known, the metrology results 242 from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work. Of course, metrology apparatus 240 and/or other metrology apparatuses (not shown) can be applied to measure properties of the processed substrates 232, 234, and incoming substrates 230.

A metrology apparatus is shown in FIG. 2(a). The stand-alone metrology apparatus 240 and/or the integrated metrology apparatus 207 may comprise such a metrology apparatus, for example, or any other suitable metrology apparatus. A target T and diffracted rays of measurement radiation used to illuminate the target are illustrated in more detail in FIG. 2(b). The metrology apparatus illustrated is of a type known as a dark field metrology apparatus. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

As shown in FIG. 2(b), target T is placed with substrate W normal to the optical axis O of objective lens 16. The substrate W may be supported by a support (not shown). A ray of measurement radiation I impinging on target T from an angle off the axis O gives rise to a zeroth order ray (solid line 0) and two first order rays (dot-chain line +1 and double dot-chain line −1). It should be remembered that with an overfilled small target, these rays are just one of many parallel rays covering the area of the substrate including metrology target T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches of the targets and the illumination angles can be designed or adjusted so that the first order rays entering the objective lens are closely aligned with the central optical axis. The rays illustrated in FIGS. 2(a) and 2(b) are shown somewhat off axis, purely to enable them to be more easily distinguished in the diagram.

At least the 0 and +1 orders diffracted by the target T on substrate W are collected by objective lens 16 and directed back through beam splitter 15. Returning to FIG. 2(a), both the first and second illumination modes are illustrated, by designating diametrically opposite apertures labeled as north (N) and south (S). When the incident ray I of measurement radiation is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction.

In the second measurement branch, optical system 20, 22 forms an image of the target T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to processor PU which processes the image, the function of which will depend on the particular type of measurements being performed. Note that the term 'image' is used here in a broad sense. An image of the grating lines as such will not be formed, if only one of the −1 and +1 orders is present.

The particular forms of aperture plate 13 and field stop 21 shown in FIG. 2 are purely examples. In another embodiment of the invention, on-axis illumination of the targets is used and an aperture stop with an off-axis aperture is used to pass substantially only one first order of diffracted light to the sensor. In yet other embodiments, $2^{nd}$, $3^{rd}$ and higher order beams (not shown in FIG. 2) can be used in measurements, instead of or in addition to the first order beams.

In order to make the measurement radiation adaptable to these different types of measurement, the aperture plate 13 may comprise a number of aperture patterns formed around a disc, which rotates to bring a desired pattern into place. Note that aperture plate 13N or 13S can only be used to measure gratings oriented in one direction (X or Y depending on the set-up). For measurement of an orthogonal grating, rotation of the target through 90° and 270° might be implemented. The use of these, and numerous other variations and applications of the apparatus are described in prior published applications, mentioned above.

FIG. 2(c) depicts a (composite) target formed on a substrate according to known practice. The target in this example comprises four gratings 25a to 25d positioned closely together so that they will all be within a measurement scene or measurement spot 24 formed by the metrology radiation illumination beam of the metrology apparatus. The four gratings thus are all simultaneously illuminated and simultaneously imaged on sensors 19 and 23. In an example dedicated to measurement of overlay, gratings 25a to 25d are themselves composite gratings formed by overlying gratings that are patterned in different layers of the semiconductor device formed on substrate W. Gratings 25a to 25d may have differently biased overlay offsets (deliberate mismatch between layers) in order to facilitate measurement of overlay between the layers in which the different parts of the composite gratings are formed. Such techniques are well known to the skilled person and will not be described further. Gratings 25a to 25d may also differ in their orientation, as shown, so as to diffract incoming radiation in X and Y directions. In one example, gratings 25a and 25c are X-direction gratings with biases of the +d, −d, respectively. Gratings 25b and 25d are Y-direction gratings with offsets +d and −d respectively. Separate images of these gratings can be identified in the image captured by sensor 23. This is only one example of a target. A target may comprise more or fewer than four gratings, or only a single grating.

FIG. 2(d) shows an example of an image that may be formed on and detected by the sensor 23, using the target of FIG. 2(c) in the apparatus of FIG. 2(a). While the pupil plane image sensor 19 cannot resolve the different individual gratings 25a to 25d, the image sensor 23 can do so. The dark rectangle represents the field of the image on the sensor, within which the illuminated spot 24 on the substrate is imaged into a corresponding circular area 26. Within this, rectangular areas 27a to 27d represent the images of the small target gratings 25a to 25d. If the targets are located in product areas, product features may also be visible in the periphery of this image field. Image processor and controller PU processes these images using pattern recognition to identify the separate images 27a to 27d of gratings 25a to 25d. In this way, the images do not have to be aligned very precisely at a specific location within the sensor frame, which greatly improves throughput of the measuring apparatus as a whole.

Once the separate images of the gratings have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an important example of such a parameter.

Presently, when performing dark field measurements using the second imaging branch, the measurement radiation used comprises only a single wavelength. The measurement radiation shows different behavior for different layers of the substrate being measured. Therefore, the wavelength of the measurement radiation should be optimized for the layer in which the target being measured is comprised. This means that the measurement radiation needs individual tuning for different measurements of targets in different layers. This takes significant time, while it is always desirable to reduce measurement time to increase fabrication productivity and/or accuracy (by allowing more measurements to be made). In addition, multilayer overlay measurements are sometimes performed, where multiple targets in different layers, are captured in a single image. For such multilayer measurements, optimization of wavelength for targets in different layers is not possible, and the wavelength chosen will only be a best compromise for the different targets.

Figure 3:
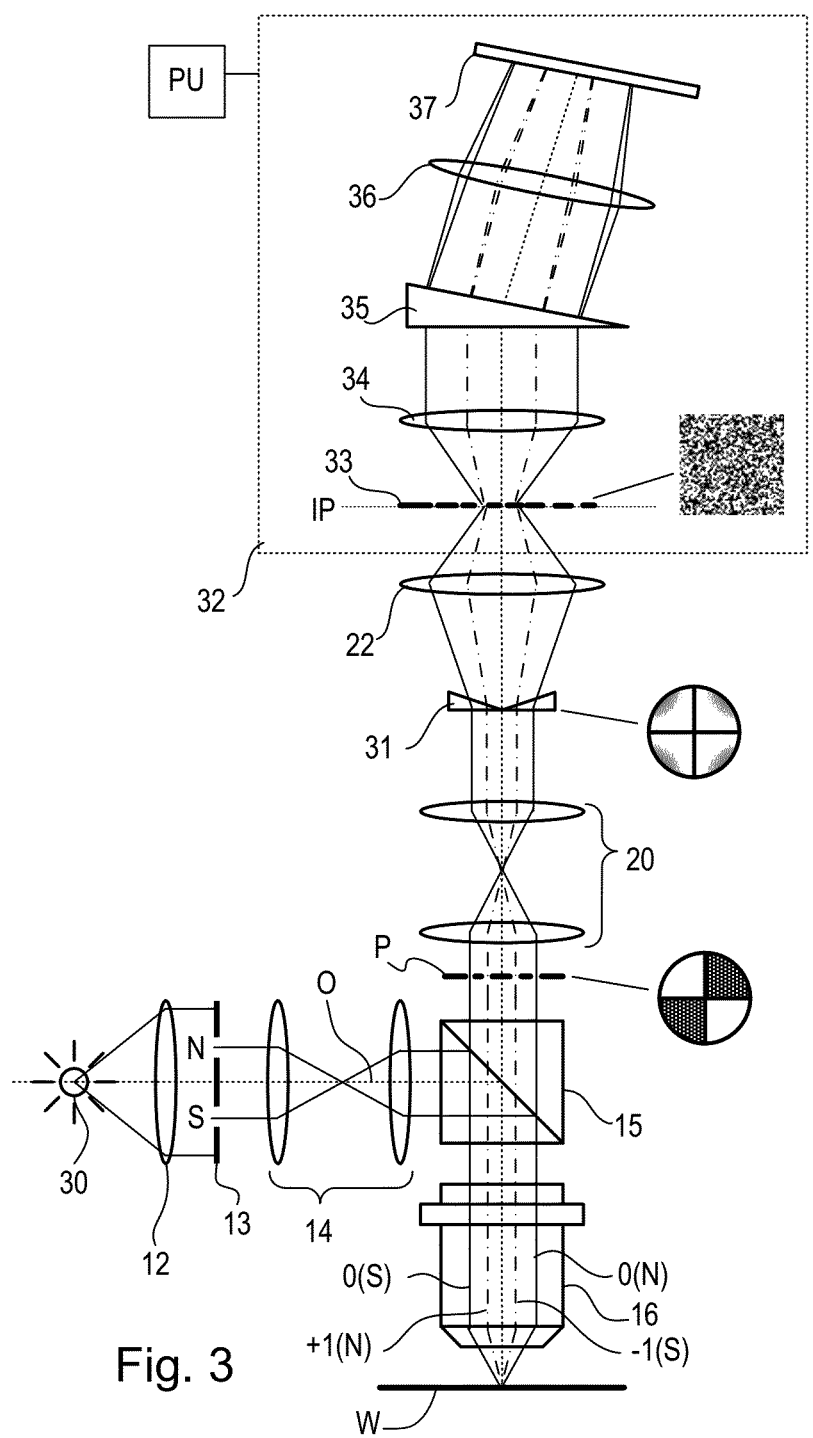
FIG. 3 comprises a schematic diagram of a metrology apparatus according to an embodiment of the invention.

FIG. 3 schematically illustrates a metrology apparatus architecture which aims to address these issues. It does this by performing measurements on a target (which may be similar to the target depicted in FIG. 2(c) for example) using multiple wavelengths in parallel. The technique used may be referred to as hyperspectral imaging. This allows selection of the optimal wavelength for each individual layer. Therefore, when performing a multilayer measurement for example, the wavelength can be optimized for each target without sacrificing throughput. Also, the provision of a complete spectral map of a target improves the robustness of the overlay measurement with respect to process variation.

The metrology apparatus is largely the same as that of the metrology apparatus of FIG. 2(a), and in particular the second measurement branch of this apparatus (Apparatuses according to this disclosure may optionally comprise another measurement branch in a similar manner to that illustrated in FIG. 2(a)). As such, the optical design principle between the illumination system and the sensor is largely unchanged, with the same numerals being attributed to equivalent elements. The optical arrangement shown in FIG. 3 is slightly different to that shown in FIG. 2(a), in that a pupil P and optical wedge element 31 arrangement is utilised to enable simultaneous imaging of the zero order and both first orders, with the optical wedge element 31 separating the images. Similar arrangements to this have been described in US20111102753, for example.

The main differences between earlier designs and the metrology apparatus of FIG. 3 are illumination system 30 and the inclusion of a hyperspectral imager, for example, a Coded Aperture Snapshot Imager (CASSI) 32, in place of sensor 23.

The illumination system 30 provides measurement radiation comprising multiple wavelengths. The measurement radiation may comprise a continuous spectrum or multiple discrete wavelengths. In an embodiment, the measurement radiation may comprise multiple wavelengths extending from 400 nm to 900 nm.

The concept of a CASSI is described in "Single disperser design for coded aperture snapshot spectral imaging" Wagadarikar A. et al, APPLIED OPTICS, Vol. 47, No. 10, 1 Apr. 2008, which is incorporated herein by reference. CASSI is a compressive sensing hyperspectral imaging technique which directly acquires an optically compressed signal rather than acquiring the full data and applying compression. The optically compressed signal is acquired by encrypting the signal with a known key (e.g., by way of a coded aperture). Knowledge of the key, which may be determined during calibration of the system, enables the original data to be estimated from the compressed signal.

CASSI 32 comprises a coded aperture 33 at the image plane (i.e., at a plane conjugate to the plane of the substrate W, which is the location of sensor 23 in the FIG. 2(a) arrangement), lens element 34, wavelength dispersive element (e.g., prism) 35, lens element 36 and sensor 37 (e.g., CCD camera) arranged in series as shown. The coded aperture 33 may comprise, for example, a binary glass mask, programmable micromirror array or a Liquid Crystal on Silicon Spatial Light Modulator (LCoS SLM). A processing unit PU (which may be part of the apparatus or separate) is provided to process the hyperspectral image.

The CASSI 32 measures a two-dimensional coded spatio-spectral projection of a three-dimensional data cube which is a 3D hyperspectral representation of a measurement scene being imaged. The spatio-spectral projection may be captured in a single snapshot, or only a few snapshots (e.g., fewer than the number of wavelengths to be measured). The measurement scene may comprise one or more structures such as targets, or parts thereof, on a substrate. The three dimensions (x, y, $\lambda$) are the two spatial directions of the target (e.g. x and y) and a spectral dimension, namely wavelength $\lambda$. A CASSI does not directly measure each voxel in the desired three-dimensional data cube. It collects a small number (relative to the size of the data cube) of coded measurements and a sparse reconstruction method is used to estimate the data cube from the noisy projections. The CASSI multiplexes spatial and spectral information from the scene into a signal detected by the sensor 37.

Coded aperture 33 modulates the spatial information over all wavelengths in the spectral cube with a coded pattern. Imaging the cube from this plane through a dispersive element 35 (e.g., a prism) disperses spectral information from each spatial location in the scene over a large area across a sensor, resulting in multiple images of the code-modulated scene at wavelength-dependent locations on the sensor 37. The spatial intensity pattern on the sensor 37 contains a coded mixture of spatial and spectral information about the scene. Note that in the specific example shown, the two first diffraction orders and the zeroth order are detected simultaneously on different areas of the sensor 37. From this multiplexed spatial intensity pattern, the 3D hyperspectral image may be restored by means of an estimation algorithm using the a priori knowledge of the coded pattern of coded aperture 33. The a priori knowledge of the coded pattern may be determined in a calibration step. Both spatial and spectral modulation is preferred for a successful estimation. Dispersion prevents all the spectral channels being modulated onto the detector with the same aperture code, while the coded aperture provides the a priori information (the key) to decrypt the detected signal.

Reconstructing a data cube from the compressed measurement relies on the assumption that the sources in the scene have piecewise smooth spatial structure, making the data cube highly compressible, e.g., on a wavelet basis. Here an example reconstruction method used to estimate the data cube from the detector measurements is described.

Defining the 3D data cube f as:

$$f = \text{vec}(F) \text{ with } F \in \mathbb{R}^{N_x \times N_y \times N_\lambda}, \quad (1)$$

where F is the matrix representation of the data cube, $N_x$ is the number of spatial channels in x, $N_y$ is the number of spatial channels in y and $N_\lambda$ is the number of spectral channels.

Then the measured signal g can be defined in terms of f and sensing matrix $\Phi$ which describes the propagation of the field in the CASSI architecture from coded aperture 33 to sensor 37:

$$g = \Phi f, \quad (2)$$

with: $\Phi \in \mathbb{R}^{N_x \cdot (N_y + N_\lambda - 1) \times N_x \cdot N_y \cdot N_\lambda}$
$f \in \mathbb{R}^{N_x \cdot N_y \cdot N_\lambda \times 1}$
$g \in \mathbb{R}^{N_x \cdot (N_y + N_\lambda - 1) \times 1}$ Therefore there are $N_x(N_y + N_\lambda - 1)$ equations and $N_x N_y N_\lambda$ unknowns.

Inversion of Equation (2) is in general impossible ($\Phi$ is underdetermined). However from sparsity property:

$$f = \Psi b \quad (3)$$

i.e., $f$ admits a sparse representation to a given frame $\Psi$ (e.g., wavelet, discrete cosine transform). Therefore, the solution of Equation (2) can be found by solving the unconstrained regularized minimization problem:

$$\hat{f} = \underset{b}{\operatorname{argmin}} \left\{ \frac{1}{2} \|g - \Phi \Psi b\|_2^2 + \tau \|b\|_1 \right\} \quad (4)$$

where $\|g - \Phi \Psi b\|_2^2$ is the error term to be minimized (e.g., a least squares error minimization) between the model and the measurement and $\tau \|b\|_1$ is the penalty term imposing sparsity of b (vector of wavelet coefficients of data cube). The reconstruction method searches for a data cube estimate with a sparse representation in the wavelet basis; i.e., a vector b that contains mostly zeros and a relatively small number of large coefficients.

The unconstrained minimization problem of Equation (4) can be reformulated as a constrained L1 minimization problem:

$$\hat{b} = \underset{b}{\operatorname{argmin}} \|b\|_1, \quad (5)$$

$$\text{s.t.} \|g - \Phi \Psi b\|_2 \leq \epsilon$$

If the signal is a 2D image an alternate recovery model implies sparsity of the gradient i.e., promoting piecewise-smooth image solutions by minimizing the Total Variation TV(f):

$$TV(f) = \sum_k \sum_{ij} \quad (6)$$
$$\underbrace{\sqrt{[f(i+1, j, k) - f(i, j, k)]^2 + [f(i, j+1, k) - f(i, j, k)]^2}}_{\text{(magnitude of the x and y gradient)}}$$

$$\hat{g} = \underset{f}{\operatorname{argmin}} [TV(f)] \text{s.t.} \|g - \Phi\|_2 \leq \epsilon \quad (7)$$

Therefore, it is aimed to find a solution for Equation (7) which implies a smooth function $f$ and is constrained to the measurement g. There are several methods possible and codes available for solving this problem. Methods include (but not limited to):

Gradient Projections for Sparse reconstructions (GPRS):
Sparse reconstruction by separable approximation (SpaRSa):
Two-step Iterative Shrinkage/Thresholding (TwIST):
Nesterov's algorithm (NESTA):
L1 regularized least squares (l1-ls):
Fast Iterative Soft-Thresholding Algorithm (FISTA):
Bregman algorithm.
Spectral projected gradient (SPGL1).

The CASSI design described herein uses a single disperser, although other designs such as those using two dispersers can also be used. However the single disperser design provides high spectral resolution over high spatial resolution and is therefore preferred in the present application.

The concepts described herein can be used to enable parallel readout of a hyperspectral measurement instead of having to select each wavelength separately and perform multiple measurements in series. Such measurements may be used, for example, in performing overlay measurements on overlay targets.

Having parallel measurements with different wavelengths make the measurements more robust. For example, better asymmetry correction can be obtained by combining multiple colors (e.g. by using blind source separation techniques).

The concepts disclosed herein may find utility beyond post-lithography measurement of structures for monitoring purposes. For example, such a detector architecture may be used in future alignment sensor concepts that are based on pupil plane detection, used in lithographic apparatuses for aligning the substrate during the patterning process.

While the targets described above are metrology targets specifically designed and formed for the purposes of measurement, in other embodiments, properties may be measured on targets which are functional parts of devices formed on the substrate. Many devices have regular, grating-like structures. The terms 'target grating' and 'target' as used herein do not require that the structure has been provided specifically for the measurement being performed.

An embodiment may include a computer program containing one or more sequences of machine-readable instructions describing methods of measuring targets on a structures and/or analyzing measurements to obtain information about a lithographic process. There may also be provided a data storage medium (e.g., semiconductor memory, magnetic or optical disk) having such a computer program stored therein. Where an existing lithography or metrology apparatus is already in production and/or in use, the invention can be implemented by the provision of updated computer program products for causing a processor to perform the methods described herein.

Further embodiments according to the present invention are described in below numbered clauses:

1. A metrology apparatus for measuring a structure formed on a substrate by a lithographic process, said metrology apparatus comprising:
an illumination system operable to provide measurement radiation comprising a plurality of wavelengths; and
a hyperspectral imager operable to obtain a hyperspectral representation of a measurement scene comprising the structure, or a part thereof, from scattered measurement radiation subsequent to said measurement radiation being scattered by said structure.

2. A metrology apparatus according to clause 1 wherein said hyperspectral representation comprises a three-dimensional data cube having two spatial dimensions and one spectral dimension.

3. A metrology apparatus according to clause 2 wherein the hyperspectral imager is a compressive sensing hyperspectral imager operable to directly acquire an optically compressed representation of said three-dimensional data cube.

4. A metrology apparatus according to clause 2 or 3 wherein the hyperspectral imager is a snapshot hyperspectral imager operable to capture the three-dimensional data cube without scanning.

5. A metrology apparatus according to clause 4 wherein the hyperspectral imager is a coded aperture snapshot spectral imager comprising a coded aperture element and at least one wavelength dispersive element, being operable to capture a two-dimensional coded spatio-spectral projection of the three-dimensional data cube.

6. A metrology apparatus according to clause 5 wherein the coded aperture element is operable to modulate spatial information of the measurement scene over all wavelengths comprised within the three-dimensional data cube with a coded pattern to obtain a coded signal; and said wavelength dispersive element is operable to disperse this coded signal spatially as a function of wavelength to obtain said two-dimensional coded spatio-spectral projection.

7. A metrology apparatus according to clause 5 or 6 comprising a processing unit operable to perform a sparse reconstruction method to estimate the three-dimensional data cube from the two-dimensional coded spatio-spectral projection and knowledge of the encoding of the coded aperture element.

8. A metrology apparatus according to clause 7 wherein said sparse reconstruction method aims to find an estimate of the three-dimensional data cube having a sparse representation.

9. A metrology apparatus according to any of clauses 5 to 8 wherein the coded aperture snapshot spectral imager is a singer disperser coded aperture snapshot spectral imager comprising only a single wavelength dispersive element.

10. A metrology apparatus according to any of clauses 5 to 9 wherein the wavelength dispersive element comprises a prism.

11. A metrology apparatus according to any of clauses 5 to 10 wherein the coded aperture element comprises a binary glass mask, programmable micromirror array or a liquid crystal on Silicon Spatial light modulator.

12. A metrology apparatus according to any preceding clause wherein the hyperspectral imager comprises a sensor for sensing said hyperspectral representation of a measurement scene.

13. A metrology apparatus according to any preceding clause wherein said illumination system is configured such that said measurement radiation comprises a continuous spectrum.

14. A metrology apparatus according to any of clauses 1 to 12 wherein said illumination system is configured such that said measurement radiation comprises a plurality of discrete wavelengths.

15. A metrology apparatus according to any preceding clause operable to measure overlay from the hyperspectral representation of the structure, said structure comprising a metrology target for the measurement of overlay.

16. An alignment sensor comprising the metrology apparatus of any preceding clause, wherein said structure comprises an alignment structure.

17. A method of measuring a structure formed on a substrate by a lithographic process comprising:
  illuminating the structure with measurement radiation comprising a plurality of wavelengths, such that the measurement radiation is scattered by the structure;
  spatially modulating the scattered measurement radiation with a coded pattern to obtain coded measurement radiation;
  spectrally dispersing the coded measurement radiation to obtain a two-dimensional coded spatio-spectral projection;
  sensing the two-dimensional coded spatio-spectral projection; and
  estimating a hyperspectral representation of the structure from the two-dimensional coded spatio-spectral projection and knowledge of the coded pattern.

18. A method according to clause 17 wherein said two-dimensional coded spatio-spectral projection is sensed during a single or few snapshot(s).

19. A method according to clause 17 or 18 wherein said hyperspectral representation comprises a three-dimensional data cube having two spatial dimensions and one spectral dimension.

20. A method according to clause 19 wherein said estimating step comprises performing a sparse reconstruction method.

21. A method according to clause 20 wherein said sparse reconstruction method aims to find an estimate of the three-dimensional data cube having a sparse representation on a defined basis.

22. A method according to any of clauses 17 to 21 wherein said measurement radiation comprises a continuous spectrum.

23. A method according to any of clauses 17 to 21 wherein said measurement radiation comprises a plurality of discrete wavelengths.

24. A method according to any of clauses 17 to 23 comprising measuring overlay from the hyperspectral representation of the structure, said structure comprising a metrology target for the measurement of overlay.

25. A lithography apparatus arranged to transfer a pattern from a patterning device onto a substrate comprising an alignment sensor according to clause 16.

26. The lithography apparatus of clause 25 comprising a substrate table constructed to hold a substrate wherein said alignment sensor is arranged to measure a position of the substrate and the lithographic apparatus includes a controller for controlling the transfer of a subsequent pattern onto the substrate at least partly by reference to the measured position.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A metrology apparatus for measuring a structure formed on a substrate by a lithographic process, said metrology apparatus comprising:
   an illumination system configured to provide measurement radiation comprising a plurality of wavelengths; and
   a hyperspectral imager configured to obtain a multi-wavelength hyperspectral representation of a measurement scene comprising the structure, or a part thereof, from scattered measurement radiation at an image plane subsequent to said measurement radiation being scattered by said structure, wherein the hyperspectral imager comprises at least one wavelength dispersive element to capture multi-wavelengths simultaneously.

2. The metrology apparatus of claim 1, wherein said hyperspectral representation comprises a three-dimensional data cube having two spatial dimensions and one spectral dimension.

3. The metrology apparatus of claim 2, wherein the hyperspectral imager is a compressive sensing hyperspectral imager configured to directly acquire an optically compressed representation of said three-dimensional data cube.

4. The metrology apparatus of claim 2, wherein the hyperspectral imager is a snapshot hyperspectral imager configured to capture the three-dimensional data cube without scanning.

5. The metrology apparatus of claim 4, wherein the hyperspectral imager is a coded aperture snapshot spectral imager comprising a coded aperture element and the at least one wavelength dispersive element is configured to capture a two-dimensional coded spatio-spectral projection of the three-dimensional data cube.

6. The metrology apparatus of claim 5, wherein the coded aperture element is configured to modulate spatial information of the measurement scene over all wavelengths comprised within the three-dimensional data cube with a coded pattern to obtain a coded signal; and said wavelength dispersive element is configured to disperse this coded signal spatially as a function of wavelength to obtain said two-dimensional coded spatio-spectral projection.

7. The metrology apparatus of claim 5, comprising a processing unit configured to perform a reconstruction method to estimate the three-dimensional data cube from the two-dimensional coded spatio-spectral projection and knowledge of the encoding of the coded aperture element.

8. The metrology apparatus of claim 7, wherein said reconstruction method aims to find an estimate of the three-dimensional data cube having a sparse representation.

9. The metrology apparatus of claim 5, wherein the coded aperture snapshot spectral imager is a single disperser coded aperture snapshot spectral imager comprising only a single wavelength dispersive element.

10. The metrology apparatus of claim 5, wherein the wavelength dispersive element comprises a prism.

11. The metrology apparatus of claim 5, wherein the coded aperture element comprises a binary glass mask, programmable micromirror array or a liquid crystal on Silicon Spatial light modulator.

12. The metrology apparatus of claim 1, wherein the hyperspectral imager comprises a sensor for sensing said hyperspectral representation of a measurement scene.

13. The metrology apparatus of claim 1, wherein said illumination system is configured such that said measurement radiation comprises a continuous spectrum.

14. The metrology apparatus of claim 1, wherein said illumination system is configured such that said measurement radiation comprises a plurality of discrete wavelengths.

15. The metrology apparatus of claim 1, configured to measure overlay from the hyperspectral representation of the structure, said structure comprising a metrology target for the measurement of overlay.

16. An alignment sensor comprising a metrology apparatus for measuring an alignment structure formed on a substrate by a lithographic process, said metrology apparatus comprising:
   an illumination system configured to provide measurement radiation comprising a plurality of wavelengths; and
   a hyperspectral imager configured to obtain a multi-wavelength hyperspectral representation of a measurement scene comprising the structure, or a part thereof, from scattered measurement radiation at an image plane subsequent to said measurement radiation being scattered by said structure, wherein the hyperspectral imager comprises at least one wavelength dispersive element to capture multi-wavelengths simultaneously.

17. A method of measuring a structure formed on a substrate by a lithographic process comprising:
   illuminating the structure with measurement radiation comprising a plurality of wavelengths, such that the measurement radiation is scattered by the structure;
   spatially modulating the scattered measurement radiation with a coded pattern to obtain coded measurement radiation;
   spectrally dispersing the coded measurement radiation to obtain a two-dimensional coded spatio-spectral projection;
   sensing, at an image plane, the two-dimensional coded spatio-spectral projection; and
   estimating, using a a hyperspectral imager, a multi-wavelength hyperspectral representation of the structure from the two-dimensional coded spatio-spectral projection and knowledge of the coded pattern, wherein the hyperspectral imager comprises at least one wavelength dispersive element to capture multi-wavelengths simultaneously.

18. The method of claim 17, wherein said two-dimensional coded spatio-spectral projection is sensed during a one or more snapshot(s).

19. The method of claim 17, wherein said hyperspectral representation comprises a three-dimensional data cube having two spatial dimensions and one spectral dimension.

20. The lithography apparatus, arranged to transfer a pattern from a patterning device onto a substrate, comprising an alignment sensor with a metrology apparatus for measuring an alignment structure formed on the substrate, said metrology apparatus comprising:
- an illumination system configured to provide measurement radiation comprising a plurality of wavelengths; and
- a hyperspectral imager configured to obtain a multi-wavelength hyperspectral representation of a measurement scene comprising the structure, or a part thereof, from scattered measurement radiation at an image plane subsequent to said measurement radiation being scattered by said structure, wherein the hyperspectral imager comprises at least one wavelength dispersive element to capture multi-wavelengths simultaneously.

* * * * *